: (12) United States Patent
Noguchi et al.

(10) Patent No.: US 7,787,692 B2
(45) Date of Patent: Aug. 31, 2010

(54) IMAGE PROCESSING APPARATUS, IMAGE PROCESSING METHOD, SHAPE DIAGNOSTIC APPARATUS, SHAPE DIAGNOSTIC METHOD AND PROGRAM

(75) Inventors: Yukinori Noguchi, Kanagawa (JP); Akira Yoda, Kanagawa (JP); Yusuke Sugimoto, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 1305 days.

(21) Appl. No.: 10/949,224

(22) Filed: Sep. 27, 2004

(65) Prior Publication Data

US 2005/0265598 A1 Dec. 1, 2005

(30) Foreign Application Priority Data

| Sep. 25, 2003 | (JP) | ............................. 2003-333053 |
| Sep. 30, 2003 | (JP) | ............................. 2003-342091 |
| Sep. 2, 2004 | (JP) | ............................. 2004-255717 |
| Sep. 2, 2004 | (JP) | ............................. 2004-255718 |

(51) Int. Cl.
*G06K 9/00* (2006.01)
(52) U.S. Cl. ....................... 382/167; 382/162; 345/582; 345/592
(58) Field of Classification Search ................. 382/167, 382/162, 165, 274, 108; 345/582–592
See application file for complete search history.

(56) References Cited

U.S. PATENT DOCUMENTS

| 4,685,071 | A * | 8/1987 | Lee ............................. 382/162 |
| 6,983,082 | B2 * | 1/2006 | Duiker ........................ 382/284 |
| 7,027,188 | B2 * | 4/2006 | Takeuchi et al. ............. 358/2.1 |
| 2003/0185459 | A1 * | 10/2003 | Takeuchi et al. ............ 382/274 |
| 2008/0221674 | A1 * | 9/2008 | Blum et al. ................. 623/5.11 |

FOREIGN PATENT DOCUMENTS

| JP | 2001-309392 A | 11/2001 |
| JP | 2002-092625 A | 3/2002 |

OTHER PUBLICATIONS

Japanese Article entitled "A three-dimensional scanner increasing its use", Nikkei Digital Engineering, June issue in 2002, No. 55 is cited and discussed on p. 2 of the specification of the above-identified application.
JP Communication, dated Feb. 16, 2010, issued in corresponding JP Application No. 2004-255717, 2 pages in Japanese.

* cited by examiner

*Primary Examiner*—Bhavesh M Mehta
*Assistant Examiner*—Sean Motsinger
(74) *Attorney, Agent, or Firm*—Sughrue Mion, PLLC

(57) ABSTRACT

An image processing apparatus for correcting an image of a subject, includes: a first illuminated image acquisition unit for acquiring the first reference member image that is an image a reference member having a plurality of normal directions taken under the first illumination condition; the second illuminated image acquisition unit for acquiring the second reference member image and a subject image that are an image of the reference member and an image of the subject, respectively, taken under the second illumination condition; a shape acquisition unit for acquiring three-dimensional shapes of the reference member and the subject; a normal direction determination unit for determining a normal direction of each region of the first reference member image, the second reference member image and the subject image based on the three-dimensional shapes of the reference member and the subject; a difference calculation unit for calculating a color difference in each region between the first and second reference member images for every normal direction; and a subject image correction unit for correcting a color of each region of the subject image with the color difference for every normal direction.

15 Claims, 14 Drawing Sheets

SUBJECT CG

ACTUAL SUBJECT IMAGE

IMAGE PROCESSING APPARATUS, IMAGE PROCESSING METHOD, SHAPE DIAGNOSTIC APPARATUS, SHAPE DIAGNOSTIC METHOD AND PROGRAM

This patent application claims priority from Japanese patent applications Nos. 2004-255717 filed on Sep. 2, 2004, 2004-255718 filed on Sep. 2, 2004, 2003-333053 filed on Sep. 25, 2003, and 2003-342091 filed on Sep. 30, 2003, the contents of which are incorporated herein by reference.

BACKGROUND OF THE INVENTION

1. Field of the Invention

The present invention relates to an image processing apparatus, an image processing method and a program. More particularly, the present invention relates to an image processing apparatus, an image processing method and a program for correcting brightness and a color of an image of a subject.

In addition, the present invention relates to a shape diagnostic apparatus, a shape diagnostic method and a program. More particularly, the present invention relates to a shape diagnostic apparatus, a shape diagnostic method and a program for detecting a defect in a shape of a subject based on an actually taken image of the subject.

2. Description of the Related Art

As a technique for adjusting a color balance in an image that is changed depending on an illumination condition when that image was taken, a technique is conventionally known in which a reference color member, such as a white or black member, and a subject are imaged simultaneously and the color balance is adjusted based on the color of the reference color member (see Japanese Patent Application Laying-Open No. 2001-309392, for example).

However, an effect of illumination on the color of the image of the subject is varied depending on a normal direction of each region of the subject. According to the above conventional technique, it was not possible to correct the color of the image appropriately depending on the normal direction of each region of the subject.

In addition, for an unknown illumination condition, it was not possible to correct the image of the subject into an image that is taken under a predetermined illumination condition.

Moreover, as a method for checking a three-dimensional shape of an object, a technique is conventionally known in which shape data of the object that was measured by a three-dimensional scanner is compared with original three-dimensional data of the object so as to check the shape of the object, for example, as described in an online article entitled "A three-dimensional scanner increasing its use", Nikkei Digital Engineering, June issue in 2002, No. 55, Nikkei Business. Publications, Inc., http://dm.nikkeibp.co.jp/free/nde/kiji/no207/report04.html (searched for on Aug. 20, 2003).

However, the three-dimensional scanner requires acquisition of huge amount of point data and huge amount of calculation for converting the point data into the shape data. Thus, the size of the object that can be measured by that three-dimensional scanner is limited. More specifically, that three-dimensional scanner cannot measure an object that is larger than a human body.

SUMMARY OF THE INVENTION

Therefore, it is an object of the present invention to provide an image processing apparatus, an image processing method, a shape diagnostic apparatus, a shape diagnostic method and a program, which are capable of overcoming the above drawbacks accompanying the conventional art. The above and other objects can be achieved by combinations described in the independent claims. The dependent claims define further advantageous and exemplary combinations of the present invention.

According to the first aspect of the present invention, an image processing apparatus for correcting an image of a subject, comprises: a first illuminated image acquisition unit operable to acquire a first reference member image that is an image of a reference member having a plurality of normal directions taken under a first illumination condition; a second illuminated image acquisition unit operable to acquire a second reference member image that is an image of the reference member taken under a second illumination condition, and a subject image that is an image of a given subject taken under the second illumination condition; a shape acquisition unit operable to acquire three-dimensional shapes of the reference member and the subject; a normal direction determination unit operable to determine a normal direction of each region in the first reference member image, the second reference member image and the subject image based on the three-dimensional shapes of the reference member and the subject; a difference calculation unit operable to calculate a color difference in each region between the first and second reference member images for every normal direction; and a subject image correction unit operable to correct a color of each region in the subject image with the color difference for every normal direction.

The reference member may be spherical.

The reference member and the subject may have substantially the same optical characteristics.

The first illuminated image acquisition unit may acquire the first reference member image under an illumination condition that is ideal for imaging the subject as the first illumination condition.

According to the second aspect of the present invention, an image processing apparatus for correcting an image of a subject, comprises: a first illuminated image generation unit operable to generate a first reference member image with a first material color under a first illumination condition, the first reference member image being a three-dimensional image of a reference member having a plurality of normal directions; a second illuminated image acquisition unit operable to acquire a subject image that is an image of a given real subject taken under a second illumination condition that is a given real illumination condition, and a second reference member image that is an image of the reference member having the same color as the subject taken under the second illumination condition; a shape acquisition unit operable to acquire three-dimensional shapes of the reference member and the subject; a normal direction determination unit operable to determine a normal direction of each region in the first reference member image, the second reference member image and the subject image based on the three-dimensional shapes of the reference member and the subject; a difference calculation unit operable to calculate a color difference in each region between the first and second reference member images for every normal direction; and a subject image correction unit operable to correct a color of each region of the subject image with the color difference for every normal direction.

According to the third aspect of the present invention, an image processing method for correcting an image of a subject, comprises: acquiring a first reference member image that is an image of a reference member having a plurality of normal directions under a first illumination condition; acquiring a second reference member image that is an image of the reference member taken under a second illumination condition, and a subject image that is an image of a given subject under the second illumination condition; acquiring three-dimensional shapes of the reference member and the subject; determining a normal direction of each region in the first reference member image, the second reference member image and the subject image based on the three-dimensional shapes of the reference member and the subject; calculating a color difference in each region between the first and second reference member images for every normal direction; and correcting a color of each region of the subject image with the color difference for every normal direction.

According to the fourth aspect of the present invention, an image processing method for correcting an image of a subject, comprises: generating a first reference member image with a first material color under a first illumination condition, the first reference member image being a three-dimensional image of a reference member having a plurality of normal directions; acquiring a subject image that is an image of a given real subject taken under a second illumination condition that is a given real illumination condition, and a second reference member image that is an image of the reference member having the same color as the subject, taken under the second illumination condition; acquiring three-dimensional shapes of the reference member and the subject; determining a normal direction of each region in the first reference member image, the second reference member image, and the subject image based on the three-dimensional shapes of the reference member and the subject; calculating a color difference in each region between the first and second reference member images for every normal direction; and correcting a color of each region of the subject image with the color difference for every normal direction.

According to the fifth aspect of the present invention, a program for use in a computer for correcting an image of a subject is provided wherein the program makes the computer execute functions of: acquiring a first reference member image that is an image of a reference member having a plurality of normal directions taken under a first illumination condition; acquiring a second reference member image that is an image of the reference member taken under a second illumination condition, and a subject image that is an image of a given subject under the second illumination condition; acquiring three-dimensional shapes of the reference member and the subject; determining a normal direction of each region in the first reference member image, the second reference member image and the subject image based on the three-dimensional shapes of the reference member and the subject; calculating a color difference in each region between the first and second reference member images for every normal direction; and correcting a color in each region of the subject image with the color difference for every normal direction.

According to the sixth aspect of the present invention, a program for use in a computer for correcting an image of a subject is provided wherein the program makes the computer execute functions of: generating a first reference member image with a first material color under a first illumination condition, the first reference member image being a three-dimensional image of a reference member having a plurality of normal directions; acquiring a subject image that is an image a given real subject taken under a second illumination condition that is a given real illumination condition, and a second reference member image that is an image of the reference member having the same color as the subject, taken under the second illumination condition; acquiring three-dimensional shapes of the reference member and the subject; determining a normal direction of each region in the first reference member image, the second reference member image, and the subject image based on the three-dimensional shapes of the reference member and the subject; calculating a color difference in each region between the first and second reference member images for every normal direction; and correcting a color of each region of the subject image with the color difference for every normal direction.

According to the present invention, it is possible to correct an image of a subject taken under a given illumination condition so as to obtain an image that is taken under a predetermined illumination condition.

Moreover, according to the seventh aspect of the present invention, a shape diagnostic apparatus for detecting a defect in a shape of a subject based on an actual image of the subject, comprises: an actual subject image acquisition unit operable to image the subject under a first illumination condition to acquire a first actual subject image; a reference member image acquisition unit operable to acquire a reference member image that is an image of a reference member having a plurality of normal directions taken under the first illumination condition; a shape acquisition unit operable to acquire original three-dimensional shapes of the reference member and the subject; a normal direction determination unit operable to determine a normal direction of each region in the reference member image based on the three-dimensional shape of the reference member; an illumination condition storage unit operable to store brightness in each region of the reference member image for every normal direction as first illumination data indicating the first illumination condition; a posture determination unit operable to determine a posture of the subject in the first actual subject image based on the original three-dimensional shape of the subject; a subject CG generation unit operable to generate a CG image of the subject, that has the original three-dimensional shape of the subject, in the posture of the subject in the first actual subject image under the first illumination condition based on the original three-dimensional shape of the subject, the first illumination data and the posture of the subject in the first actual subject image; and a defective region detection unit operable to compare the CG image with the first actual subject image for every region to detect a region where a brightness difference exceeds a predetermined reference value as a defective region.

The shape diagnostic apparatus may further comprise a unit operable to determine a normal direction corresponding to brightness of the defective region from the first illumination data, and determine a three-dimensional shape of the defective region based on the determined normal direction.

The reference member may be spherical.

The reference member and the subject may have substantially the same optical characteristics.

According to the eight aspect of the present invention, a shape diagnostic apparatus for detecting a defect in a shape of a subject based on an image of a subject actually taken, comprises: an actual subject image acquisition unit operable to acquire a first actual subject image that is an image of the subject taken under a first illumination condition; an illumination condition storage unit operable to store the first illumination condition; a three-dimensional shape acquisition unit operable to acquire an original three-dimensional shape of the subject and optical characteristics of the subject; a posture determination unit operable to determine a posture of the subject in the first actual subject image based on the original three-dimensional shape of the subject; a subject CG generation unit operable to generate a first CG image of the subject based on the posture of the subject in the first actual subject image, the first illumination condition, and the optical characteristics and the original three-dimensional shape of the subject; and a defective region detection unit operable to compare the first CG image of the subject with the first actual subject image for each region to detect a region where a brightness difference exceeds a predetermined reference value as a defective region.

The actual subject image acquisition unit may further acquire a second actual subject image that is an image of the subject taken under a second illumination condition having a different illumination direction from that of the first illumination condition. The illumination condition storage unit may further store the second illumination condition. The posture determination unit may further determine the posture of the subject in the second actual subject image based on the original three-dimensional shape of the subject. The subject CO generation unit further generates a second CG image of the subject based on the posture of the subject in the second actual subject image, the second illumination condition, and the optical characteristics and the original three-dimensional shape of the subject. The defective region detection unit further compares the second CG image of the subject with the second actual subject image for each region and further detects a region where a brightness difference exceeds a predetermined reference value as a defective region.

The second illumination direction may have an illumination direction that is perpendicular to that of the first illumination condition.

The shape diagnostic apparatus may further comprise: a charge unit operable to charge the subject; and a spray unit operable to spray colored particles, that are attracted and adhere to a charged object, to the charged subject, wherein the actual subject image acquisition unit images the subject with the colored particles adhering thereto to further acquire a third actual subject image, the subject CG generation unit acquires optical characteristics of the subject with the colored particles and further generates a third CG image of the subject based on the posture of the subject in the third actual subject image, the first illumination condition, the optical characteristics of the subject with the colored particles, and the original three-dimensional shape of the subject, and the defective region detection unit further compares the third CG image of the subject with the third actual subject image for each region to detect a region where a brightness difference exceeds a predetermined reference value as a defective region.

According to the ninth aspect of the present invention, a shape diagnostic method for detecting a defect in a shape of a subject based on an actual image of an subject, comprises: acquiring an actual subject image that is an image of the subject taken under a first illumination condition; acquiring a reference member image that is an image of a reference member having a plurality of normal directions, taken under the first illumination condition; acquiring original three-dimensional shapes of the reference member and the subject; determining a normal direction of each region in the reference member image based on the three-dimensional shape of the reference member; storing brightness of each region of the reference member image for every normal direction as first illumination data indicating the first illumination condition; determining a posture of the subject in the actual subject image based on the three-dimensional shape of the subject; generating a CG image of the subject, that has the original three-dimensional shape of the subject, in the posture of the subject in the actual subject image under the first illumination condition based on the original three-dimensional shape, the first illumination data and the posture; and comparing the CG image of the subject with the actual subject image for each region to detect a region where a brightness difference exceeds a predetermined reference value as a defective region.

According to the tenth aspect of the present invention, a shape diagnostic method for detecting a defect in a shape of a subject based on an actual image of the subject, comprises: acquiring a first actual subject image that is an image of the subject taken under a first illumination condition; storing the first illumination condition; acquiring an original three-dimensional shape and optical characteristics of the subject; determining a posture of the subject in the first actual subject image based on the original three-dimensional shape of the subject; generating a first CG image of the subject based on a posture of the subject in the first actual subject image, the first illumination condition, and the optical characteristics and the original three-dimensional shape of the subject; and comparing the first CG image of the subject with the first actual subject image for each region to detect a region where a brightness difference exceeds a predetermined reference value as a defective region.

According to the eleventh aspect of the present invention, a program for use in a computer for detecting a defect in a shape of a subject based on an actual image of the subject is provided wherein the program makes the computer execute functions of: acquiring an actual subject image that is an image of the subject taken under a first illumination condition; acquiring a reference member image that is an image of a reference member having a plurality of normal directions under the first illumination condition; acquiring original three-dimensional shapes of the reference member and the subject; determining a normal direction of each region of the reference member image based on the three-dimensional shape of the reference member; storing brightness in respective regions of the reference member image for every normal direction as first illumination data indicating the first illumination condition; determining a posture of the subject in the actual subject image based on the three-dimensional shape of the subject; generating a CG image of the subject to have the original three-dimensional shape of the subject, in the posture of the subject in the actual subject image under the first illumination condition based on the original three-dimensional shape of the subject, the first illumination data and the posture of the subject in the actual subject image; and comparing the CG image of the subject with the actual subject image to detect a region where a brightness difference exceeds a predetermined reference value as a defective region.

According to the twelfth aspect of the present invention, a program for use in a computer for detecting a defect in a shape of a subject based on an actual image of the subject is provided, wherein the program makes the computer execute functions of: acquiring a first actual subject image that is an image of the subject taken under a first illumination condition; storing the first illumination condition; acquiring an original three-dimensional shape of the subject and optical characteristics of the subject; determining a posture of the subject in the first actual subject image based on the original three-dimensional shape of the subject; generating a first CG image of the subject based on the posture of the subject in the first actual subject image, the first illumination condition, and the optical characteristics and the original three-dimensional shape of the subject; and comparing the first CG image of the subject with the first actual subject image for each region to detect a region where a brightness difference exceeds a predetermined reference value as a defective region.

According to the present invention, it is possible to detect a defect in a shape of a subject based on an actually taken image of the subject.

The summary of the invention does not necessarily describe all necessary features of the present invention. The present invention may also be a sub-combination of the features described above. The above and other features and advantages of the present invention will become more apparent from the following description of the embodiments taken in conjunction with the accompanying drawings.

DETAILED DESCRIPTION OF THE INVENTION

The invention will now be described based on the preferred embodiments, which do not intend to limit the scope of the present invention, but exemplify the invention. All of the features and the combinations thereof described in the embodiment are not necessarily essential to the invention.

Embodiment 1

Figure 1:
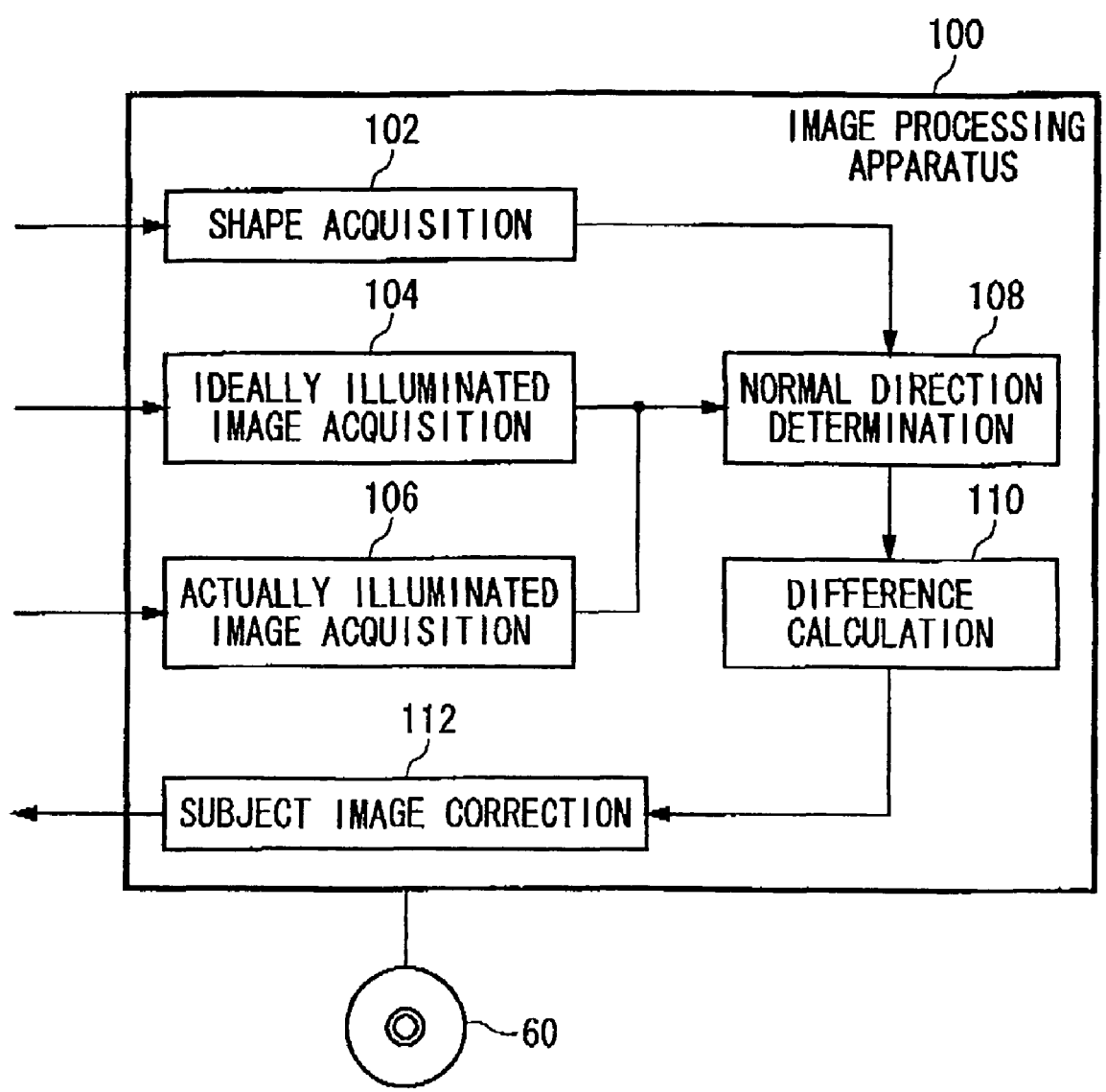
FIG. 1 is a functional block diagram of an image processing apparatus 100 according to the present invention.

FIG. 1 is a functional diagram of an image processing apparatus 100 according to the first embodiment of the present invention. It is an object of the image processing apparatus 100 to correct an image of a subject that was taken under a given illumination condition so as to obtain an image that is taken under a predetermined illumination condition. In this embodiment, two examples of the image processing apparatus 100 are described. In the first example, in order to determine the illumination condition, a reference member having a plurality of normal directions are imaged. By imaging such a reference member, it is possible to simultaneously image planes arranged at various angles with respect to illumination light. In the second example, a three-dimensional image of the reference member is generated with a virtual material color under a virtual illumination condition. In the following description, the first example is mainly described. For the second example, only the structure or operation different from that in the first example is described. In the second example, same components as those in the first example are labeled with the same reference numerals and the description thereof is omitted.

It is desirable that the reference member be spherical. In the present embodiment, a spherical reference ball 10 is used as the reference member. Since the reference ball 10 is spherical, it includes planes having all normal directions. Therefore, by using such a reference ball 10, it is possible to efficiently take or generate an image corresponding to any normal direction. Moreover, it is preferable that optical characteristics of the reference member and those of the subject be substantially the same. In this case, it is possible to determine an optical effect of the illumination condition on the subject equivalently by using the reference member.

In the first example, the image processing apparatus 100 includes: an ideally illuminated image acquisition unit 104 that acquires an "ideal ball image" that is an image of the reference ball 10 taken under an illumination condition that is ideal for imaging of the subject (hereinafter, referred to as "ideal illumination condition"); an actually illuminated image acquisition unit 106 that acquires an "actual ball image" that is an image of the reference ball 10 taken under a given real illumination condition (hereinafter, referred to as an "actual illumination condition") and an "actual subject image" that is an image of the subject taken under the "actual illuminated condition"; a shape acquisition unit 102 that acquires the three-dimensional shapes of the reference ball 10 and the subject; a normal direction detection unit 108 that determines normal directions of respective regions in the "ideal ball image", the "actual ball image" and the "actual subject image" based on the three-dimensional shapes of the reference ball 10 and the subject; a difference calculation unit 110 that calculates a color difference in each region between the "ideal ball image" and the "actual ball image" for every normal direction; and a subject image correction unit 112 that corrects the color of each region of the "actual subject image" with the color difference for every normal direction.

The "ideal illumination condition" is an exemplary first illumination condition of the present invention and the "ideal ball image" is an exemplary first reference member image of the present invention. The "actual illumination condition" is an exemplary second illumination condition of the present invention and the "actual ball image" is an exemplary second reference member image of the present invention. Moreover, the ideally illuminated image acquisition unit 104 is an exemplary first illuminated image acquisition unit of the present invention and the actually illuminated image acquisition unit 106 is an exemplary second illuminated image acquisition unit of the present invention.

In the second example, the ideally illuminated image acquisition unit 104 generates a three-dimensional image of the reference ball 10 with a "specified Color" under the "ideal illumination condition" so as to obtain an "ideal ball image". That is, the ideal ball image in the second example is a computer graphics (CG) image of the reference ball 10 generated by the image processing apparatus 100. The ideally illuminated image acquisition unit 104 in the second example is an example of the first illuminated image generation unit of the present invention. The ideal illumination condition contains an illumination condition that is necessary for generation of the ideal ball image, such as spectral distribution of illumination and the position of illumination. The actually illuminated image acquisition unit 106 in the second example images a given real subject under the actual illumination condition that is a given real illumination condition, thereby acquiring an "actual subject image". The actually illuminated image acquisition unit 106 further acquires the "actual ball image" that is an image of the reference ball 10 having the same color as the subject under the above actual illumination condition. The difference calculation unit 110 calculates a color difference in each region between the "ideal ball image" and the "actual ball image" for every normal direction. The subject image correction unit 112 corrects the color of each region of the "actual subject image" with the color difference calculated by the difference calculation unit 110 for every normal direction.

A recording medium 60 stores a program that makes the image processing apparatus 100 execute the functions of the shape acquisition unit 102, ideally illuminated image acquisition unit 104, actually illuminated image acquisition unit 106, normal direction detection unit 108, difference calculation unit 110 and subject image correction unit 112. The image processing apparatus 100 may acquire such a program via a network and execute it.

By the aforementioned structure, the image processing apparatus 100 of the first example can calculate a difference of color between the "ideal ball image" and the "actual ball image" for every normal direction as a "color difference" caused by the difference between the "ideal illumination condition" and the "actual illumination condition". Then, by correcting the "actual subject image" with the "color difference", it is possible to obtain an image in a case where the subject is imaged under the "ideal illumination condition". In other words, the image processing apparatus 100 of the first example can correct an image of the subject that was taken under a given illumination condition into an image that is taken under the "ideal illumination condition".

In the second example, the image processing apparatus 100 calculates the difference of the color between the "ideal ball image" and the "actual ball image" for every normal direction as a color difference caused by the difference between the "ideal illumination condition" and the "actual illumination condition" and a difference between the "specified color" and an "actual color of the real reference ball 10". Then, by correcting the "actual subject image" with the above color difference, it is possible to acquire an image in a case where the subject of the "specified color" is taken under the "ideal illumination condition". In other words, the image processing apparatus 100 of the second example can generate an image of the subject of the "specified color" that is taken under the "ideal illumination condition" from the subject image that was taken under a given illumination condition.

Figure 2:
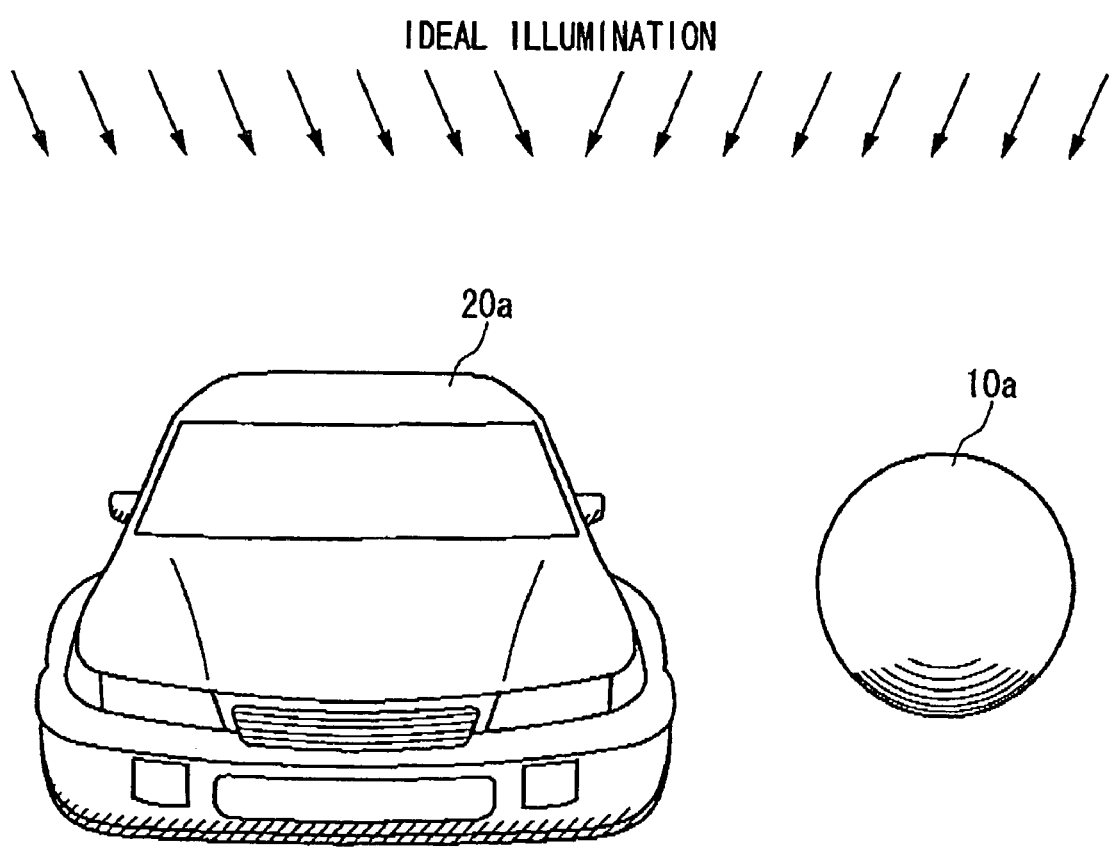
FIG. 2 shows acquisition of an "ideal ball image".

FIG. 2 shows how the ideally illuminated image acquisition unit 104 of the first example acquires the "ideal ball image". The "ideal ball image" is acquired by imaging the reference ball 10 under the same condition as the "ideal illumination condition" in which an ideal subject image 20*a* that is ideal in a case of imaging an automobile as the subject 20, for example. The "ideal illumination condition" is obtained, for example, by placing the subject 20 in a studio or a showroom and adjusting spectral components of illumination, the number of lights, the angle, intensity and distance of illumination, and the like, so as to be most appropriate for the appearance of the subject 20. In this imaging, the illumination condition for the reference ball 10 and the subject 20 is the same for every normal direction.

On the other hand, the ideally illuminated image acquisition unit 104 of the second example generates three-dimensional CG images of the subject 20 and the reference ball 10 with the same color under the same illumination condition and displays the generated three-dimensional CC images on a monitor. A user adjusts the color and the illumination condition while looking the image of the subject 20 displayed on the monitor, and determines the color and the illumination condition when a desired appearance of the subject 20 is obtained. At this time, the ideally illuminated image acquisition unit 104 acquires the image of the reference ball 10 when the color and illumination condition were determined as an "ideal ball image".

Figure 3:
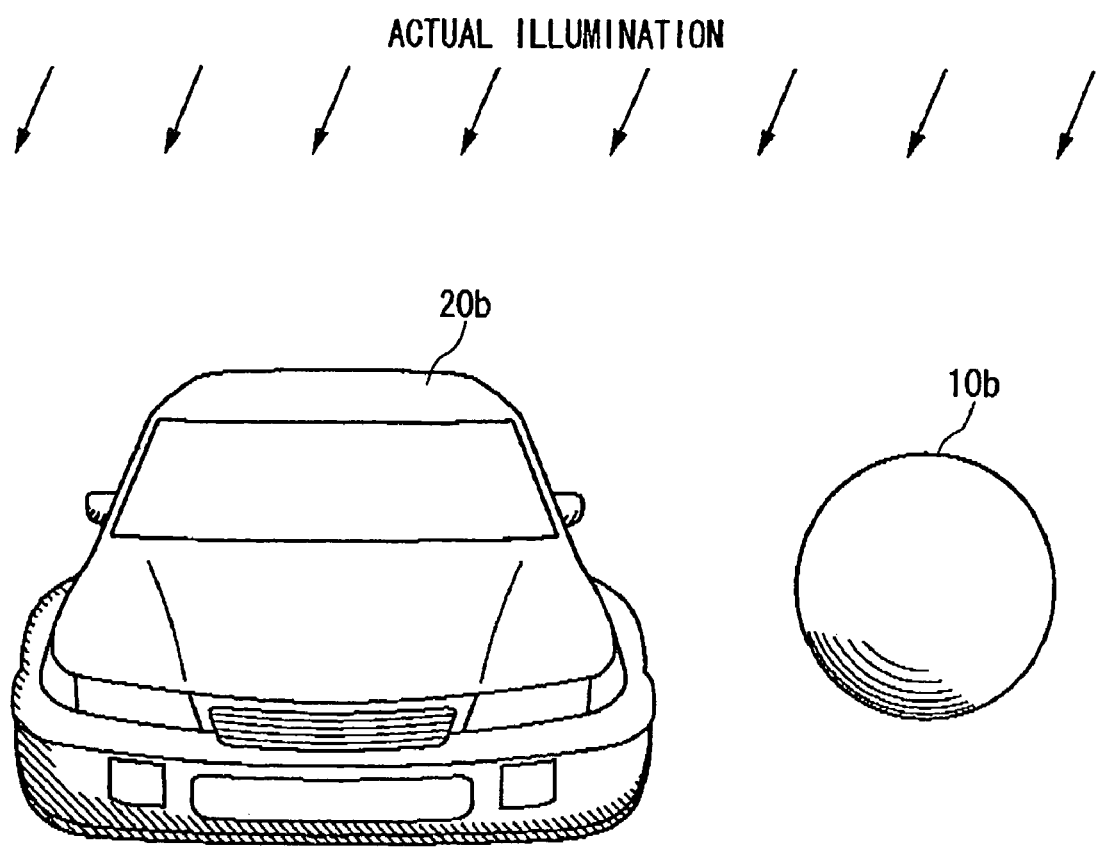
FIG. 3 shows acquisition of an "actual subject image" and an "actual ball image" under an "actual illumination condition".

FIG. 3 shows acquisition of the "actual subject image" and the "actual ball image" under the "actual illumination condition". The "actual illumination condition" is an imaging condition in a case where a used car dealer or an owner who wishes to sell an automobile as the subject 20 takes an image of the subject 20 indoors or outdoors in order to place that image on a site of user-car information. The "actual illumination condition" is a given illumination condition. In the "actual illumination condition", the spectral components, angle and intensity of illumination, and the like, are not adjusted to be ideal, unlike the "ideal illumination condition". For example, in this example, the "actual illumination condition" has illumination lower than that in the "ideal illumination condition", and the direction of illumination in the "actual illumination condition" is not balanced, as compared with the "ideal illumination condition". Thus, the "actual subject image" taken under the "actual illumination condition" is generally darker and has a broader shadow, as compared with an image of the subject that is taken under the "ideal illumination condition".

In this case, the illumination condition for the reference ball 10 and that for the subject 20 are the same for every normal direction. The actually illuminated image acquisition unit 106 images the subject 20 and the reference ball 10 simultaneously in this state, thereby acquiring the "actual subject image" and the "actual ball image" that were taken under the same "actual illumination condition".

In the shown example, the reference ball 10 is imaged together with the subject 20. However, the reference ball 10 may be imaged separately from the subject 20 as long as the reference ball 10 is imaged under the same illumination condition as that for the subject 20. For example, the reference ball 10 may be imaged immediately before or after the imaging of the subject 20 under the same illumination condition as that for the subject 20.

Figure 4:
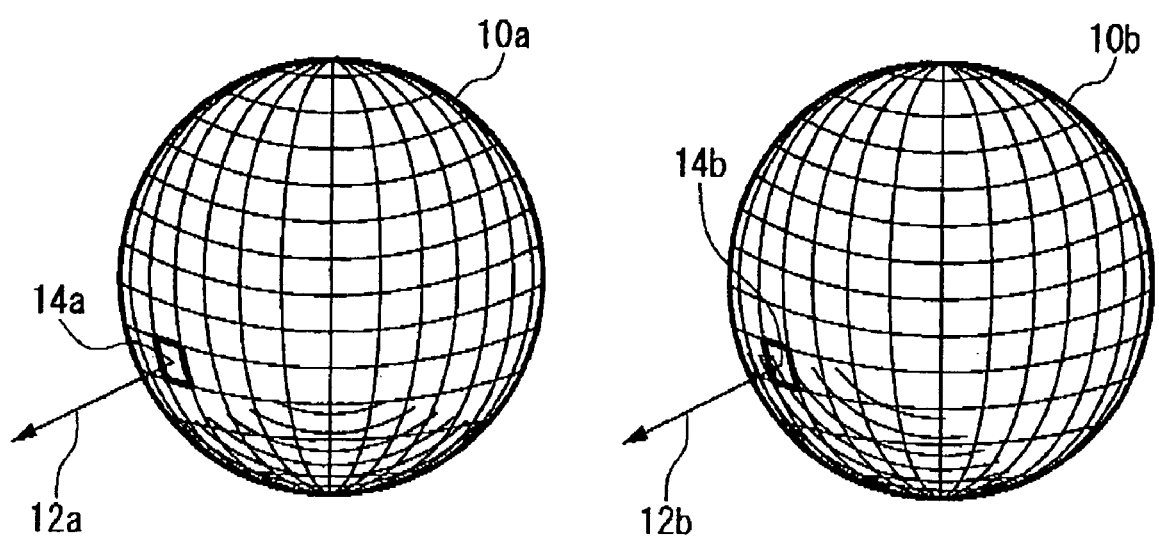
FIG. 4 shows an exemplary method for determining normal directions of the "ideal ball image" and the "actual ball image".

FIG. 4 shows an exemplary method for determining normal directions of the "ideal ball image" and the "actual ball image". The normal direction detection unit 108 acquires shape data of the reference ball 10 from the shape acquisition unit 102 and superimposes the acquired shape data on each of the ideal ball image 10*a* and the actual ball image 10*b*, thereby determining the normal directions of respective regions. Since the reference ball 10 of the present embodiment is spherical, the shape of image data is the same irrespective of the imaging direction. Therefore, the normal direction detection unit 108 can superimpose the shape data on each of the ideal ball image 10*a* and the actual ball image 10*b* easily.

The shape data representing the three-dimensional shape is wireframe data, for example. The wireframe data represents a shape of an object as collection of small planes and defines a normal direction on each small plane. The normal direction detection unit 108 determines the normal direction defined for each of the small planes of the wireframe data as a normal direction in a corresponding region of each of the ideal ball image boa and the actual ball image 10*b*. The format of the shape data is not limited to wireframe. The shape data may be any of polygon data, surface data and solid data, as long as it allows the normal direction of each region to be read out.

Then, the difference calculation unit 110 of the first example compares colors of regions having the same normal direction in the ideal ball image 10*a* and the actual ball image 10*b*, and calculates a color difference obtained as a result of the comparison for every normal direction. For example, in FIG. 4, a normal 12*a* in the ideal ball image 10*a* and a normal 12*b* in the actual ball image 10*b* are the same. The difference calculation unit 110 compares a color of a small plane 14*a* with a color of a small plane 14*b* having the same normal direction as the small plane 14*a*, and stores a color difference to correspond to the direction of the normal 12*a*, 12*b*. The color difference is represented by differences of R, G and B values and a magnifying power, for example. Alternatively, the color difference may be a difference or a magnifying power of each parameter in L*a*b* color system or L*C*h* color system.

Figure 5A:
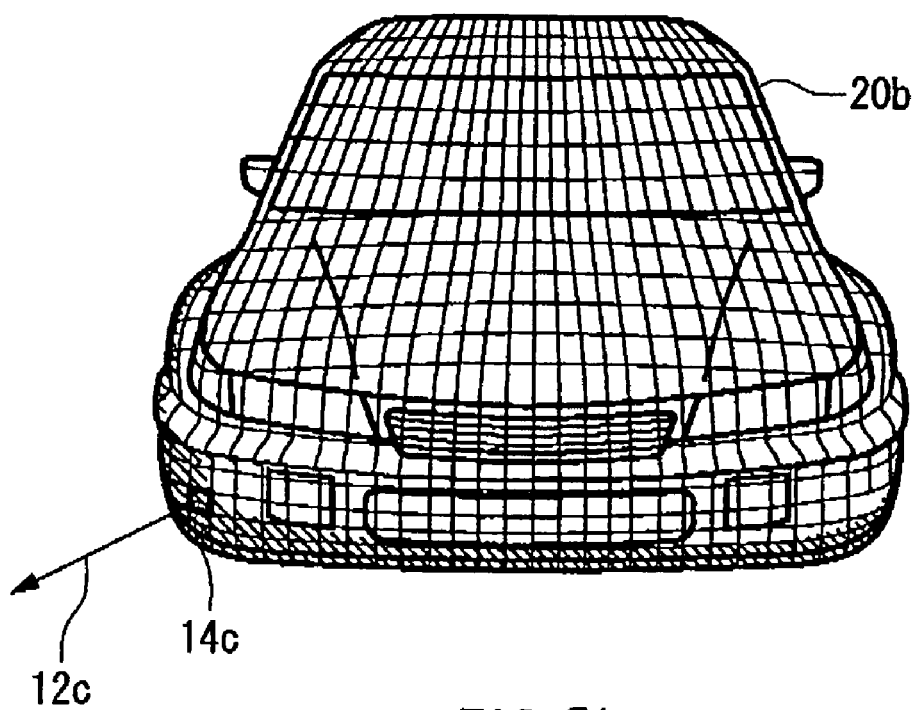
FIGS. 5A and 5B show an example of correction of the actual subject image taken under the "actual illumination condition" with a color difference.
Figure 5B:
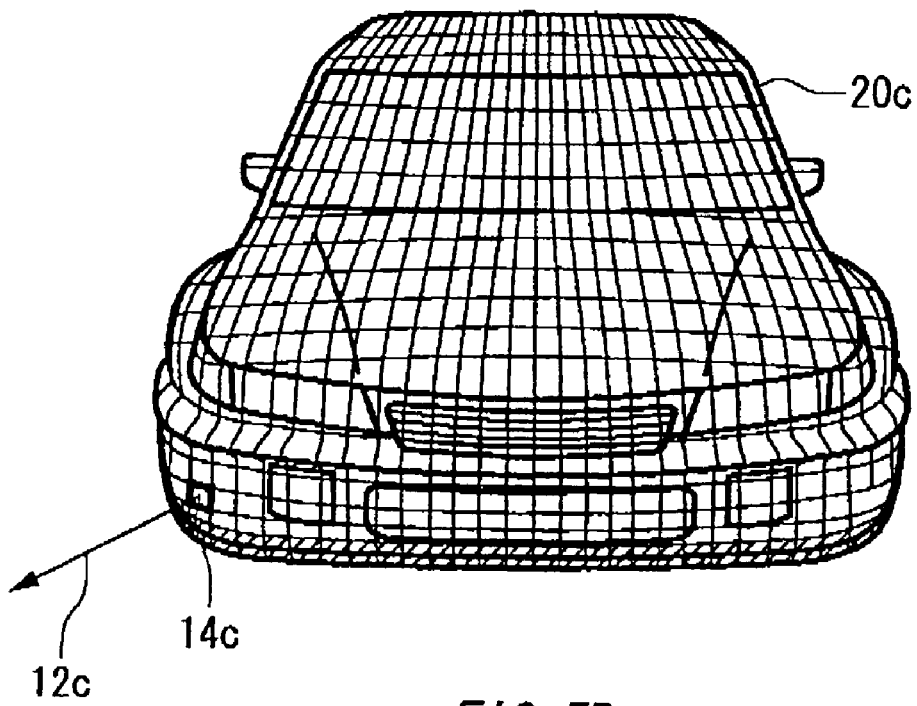

FIGS. 5A and 5B show an example of correction of the actual subject image taken under the "actual illumination condition" with the aforementioned color difference. FIG. 5A shows an actual subject image 20 taken under the "actual illumination condition". The normal direction detection unit 108 acquires the shape data of the subject 20 representing the three-dimensional shape thereof and the actual subject image 20*b* and determines a normal direction of each region of the actual subject image 20*b*. In a case where the shape of the subject is not spherical, the normal direction detection unit 108 superimposes the shape data on the actual subject image 20*b* in such a manner that the profile of the shape data is the most coincident with the actual subject image 20*b*. A method for determining the normal direction of each region after the shape data was superimposed on the actual subject image 20*b* is the same as the method for determining the normal direction of the reference ball 10, that was described referring to FIG. 4. Therefore, the determination method of the normal direction is omitted here.

The subject image correction unit 112 corrects a color and brightness of the actual subject image 20*b* for every normal direction of the actual subject image 20*b* so as to remove the "color difference" calculated by the difference calculation unit 110. For example, the direction of the normal 12*c* is the same as that of the normals 12*a* and 12*b* in FIG. 4. In this case, the subject image correction unit 112 subtracts a color difference of the small plane 14*b* with respect to the small plane 14*a* from the color of the small plane 14*c* having the normal 12*c*. As a result, a corrected subject image 20*c* shown in FIG. 5B is obtained.

Please note that in the first example, the "color difference" for each normal direction is caused by a difference between the "ideal illumination condition" and the "actual illumination condition". Thus, by subtracting the "color difference" from the actual subject image 20*b*, the actual subject image that was taken under the "actual illumination condition" can be corrected into the corrected subject image 20*c* that is an image in a case where the subject is imaged under the "ideal illumination condition".

Moreover, in the second example, the "color difference" for each normal direction is caused by the difference between the "ideal illumination condition" and the "actual illumination condition" and the difference between the "specified color" and the "color of the real reference ball 10". Thus, by subtracting the "color difference" from the actual subject image 20*b*, the actual subject image can be corrected into the corrected subject image 20*c* that is an image in a case where the subject is imaged under the "ideal illumination condition" to have the "specified color"

Figure 6:
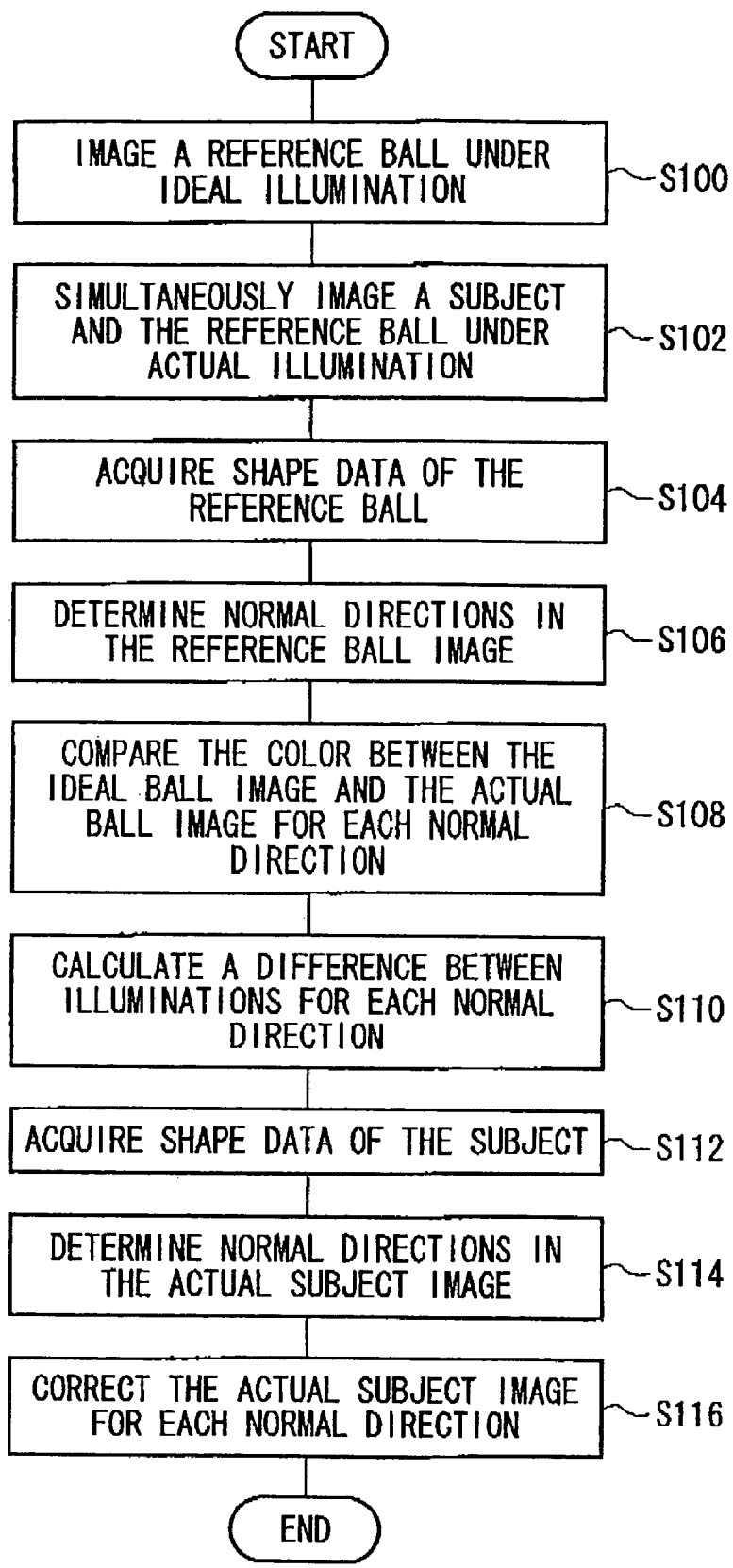
FIG. 6 is a flowchart for generating an image of the subject that is taken under an ideal illumination condition from the "actual subject image".

FIG. 6 is a flowchart in a case of correcting an "actual subject image" taken under a given illumination condition into an image in a case where the subject is imaged under the ideal illumination condition. First, the ideally illuminated image acquisition unit 104 images the reference ball under the ideal illumination condition that is ideal for that subject, so as to acquire an ideal ball image (Step S100). Then, the actually illuminated image acquisition unit 106 simultaneously images the subject and the reference ball under a given actual illumination condition, thereby acquiring an actual subject image and an actual ball image (Step S102).

Then, the shape acquisition unit 102 acquires shape data representing the three-dimensional shape of the reference ball (Step S104). The normal direction detection unit 108 then superimposes the shape data on each of the ideal ball image and the actual ball image so as to determine normal directions of corresponding regions (Step S106). Then, the difference calculation unit 110 compares the color of the reference ball between the ideal ball image and the actual ball image for every normal direction (Step S108), thereby calculating a "color difference" for every normal direction (Step S110).

Next, the normal direction detection unit 108 acquires shape data representing the three-dimensional shape of the subject (Step S112). Then, the normal direction detection unit 108 superimposes the shape data on the actual subject image in such a manner that their orientations are coincident with each other, thereby determining the normal directions of respective regions of the actual subject image (Step S114). In order to make the orientations of the shape data and the actual subject image coincident with each other, the orientation of the shape data is gradually changed so as to find an orientation when the profile of the shape data is the most coincident with the actual subject image, for example.

Finally, the subject image correction unit 112 removes the "color difference" calculated by the difference calculation unit 110 from the actual subject image for every normal direction of the actual subject image. In this manner, it is possible to obtain a corrected subject image that is an image in a case where the subject is imaged under the "ideal illuminated condition" from the actual subject image that was taken under the "actual illumination condition" (Step S116). That is the end of this flow.

Figure 7:
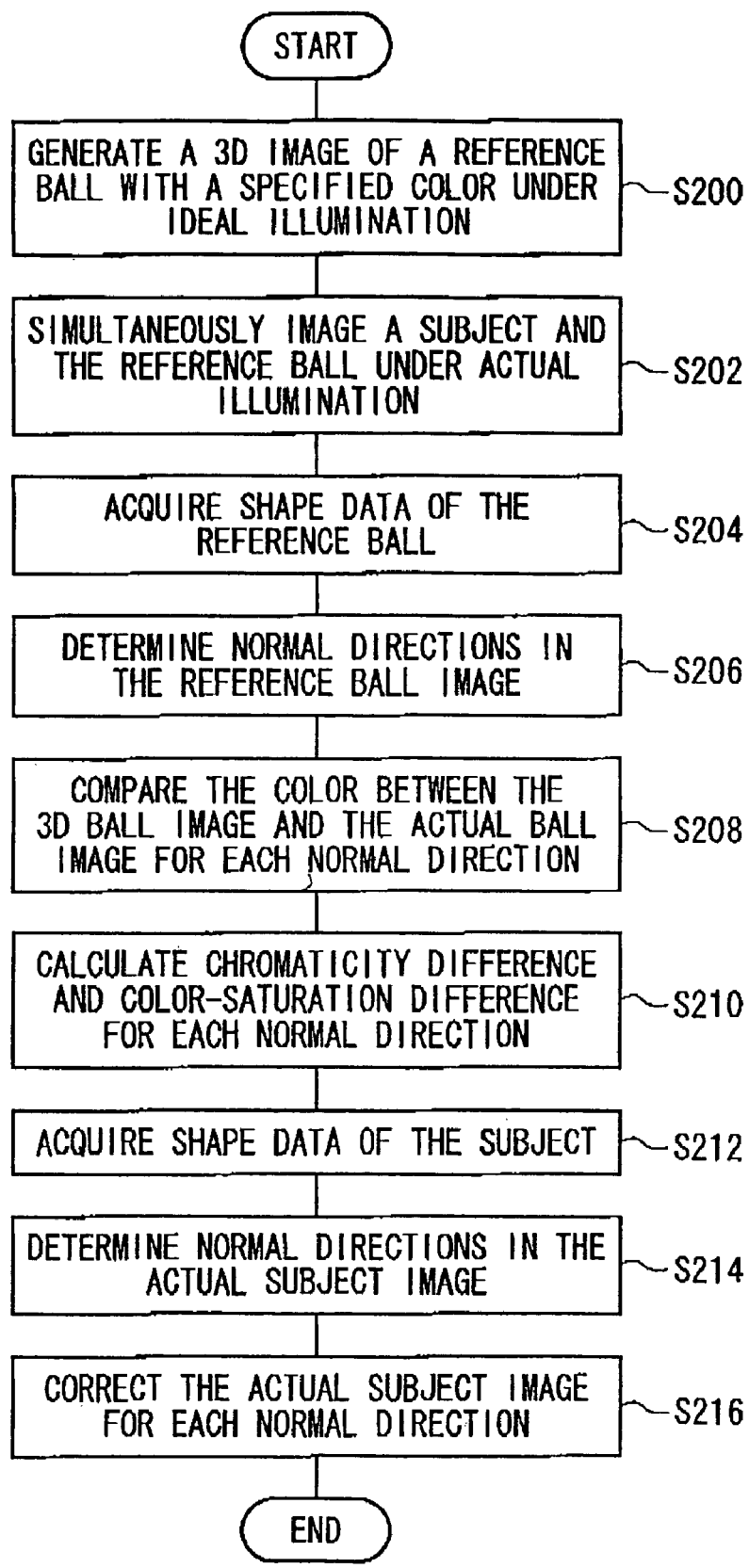
FIG. 7 is a flow chart of generating an image of the subject in the "actual subject image", that is taken under the ideal illumination condition to have a specified color.

FIG. 7 is a flowchart for generating an image obtained by changing the color of the subject in the "actual subject image" taken under a given illuminated condition to a specified color in such a manner that the generated image corresponds to an image taken under the ideal illumination condition. First, the ideally illuminated image acquisition unit 104 generates a three-dimensional image of the reference ball 10 with a "specified color" under the "ideal illumination condition", thereby obtaining an "ideal ball image" (Step S200). Steps S202, S204 and S206 following to Step S200 are the same as Steps S102, S104 and S106 described before and therefore the description of those steps is omitted. Next, the difference calculation unit 110 compares the color of the reference ball 10 between the ideal ball image that is the 3D image and the actual ball image for every normal direction (Step S208), thereby calculating a difference of "chromaticity" and a difference of "color saturation" (Step S210). Steps S212 and S214 following to Step S210 are the same as Steps S112 and S114 described before and therefore the description of those steps is omitted.

Finally, the subject image correction unit 112 removes the "color difference" calculated by the difference calculation unit 11 from the actual subject image for every normal direction of the actual subject image. As a result, the image in a case where the subject in the "actual subject image" taken under a given illumination condition is changed to have the specified color and it is assumed that the subject is imaged under the ideal illumination condition, is generated (Step S216). That is the end of this flow.

As described above, according to the present embodiment, it is possible to correct an image of a subject taken under a given illumination condition into an image that is taken under a predetermined illumination condition.

Embodiment 2

Figure 8:
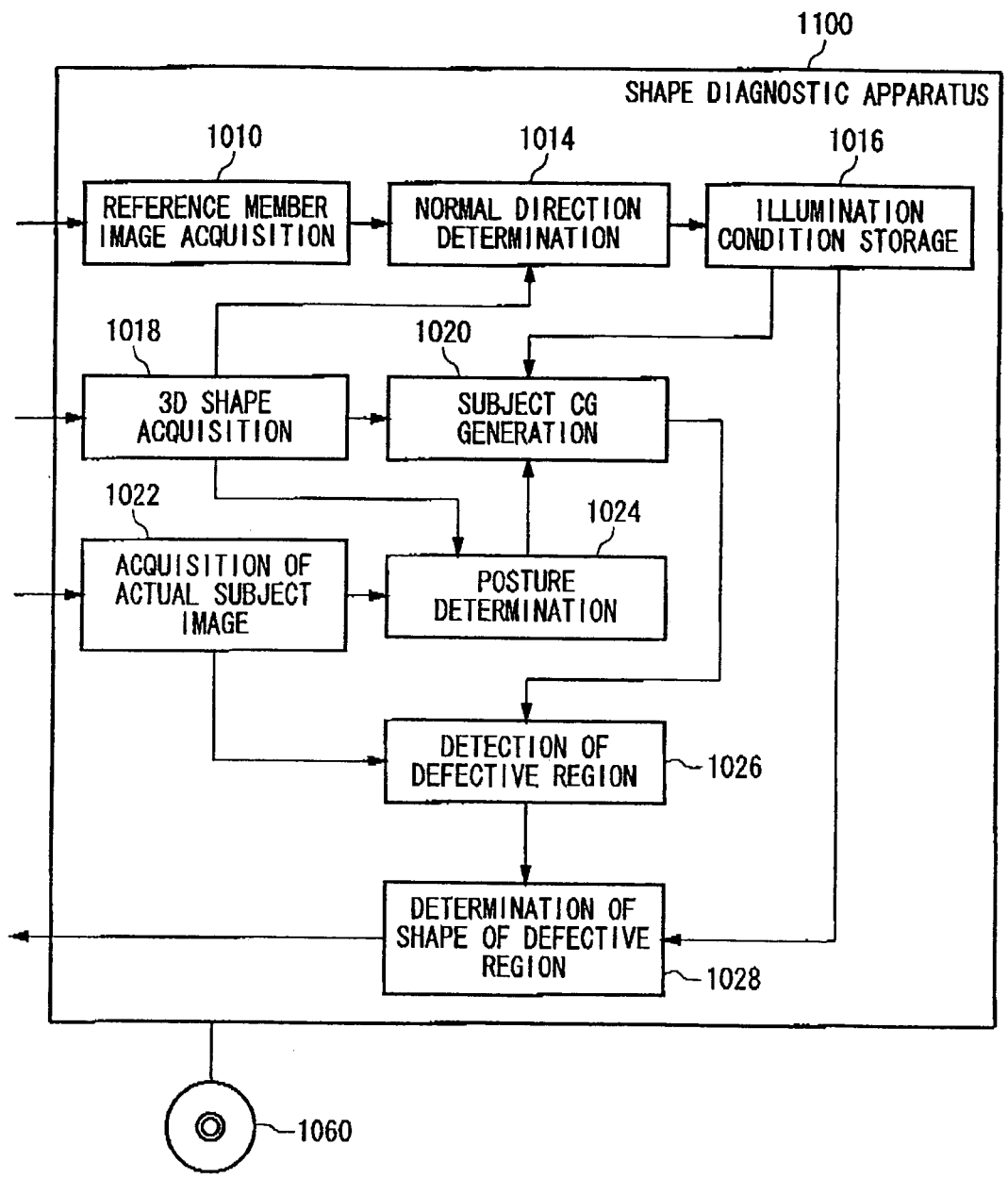
FIG. 8 is a functional block diagram of a shape diagnostic apparatus 1100 according to the present invention.

FIG. 8 is a functional diagram of a shape diagnostic apparatus 1100 according to an embodiment of the present invention. The shape diagnostic apparatus 1100 aims to detect a defect in a shape of a subject based on an actually taken image of the subject. In a case where the color of the subject is uniform, brightness in each region of the subject when the subject was imaged under a given illumination condition depends on the orientation of a plane of that region, i.e., a normal direction of that region. Thus, in the present embodiment, the shape diagnostic apparatus 1100 generates a CG image of the subject in the same posture as that in the actual image under the same illumination condition as that for the actual image of the subject, and compares the CG image with the actual image. When a brightness difference between the actual image and the CC image exceeds a predetermined reference value in a certain region, it is determined that the normal direction of that region is abnormal, i.e., the shape of that region has a defect.

In order to determine the illumination condition for the subject, the shape diagnostic apparatus 1100 images a reference member having a plurality of normal directions. The shape diagnostic apparatus 1100 can simultaneously image planes respectively having different normal directions by imaging the reference member having a plurality of normal directions.

Especially, the three-dimensional shape of the reference member is preferably spherical. In a case where the reference member is a spherical member, it is possible to efficiently image planes having all possible normal directions. Moreover, it is desirable that optical characteristics of the reference member be the same as those of the subject. In this case, the illumination condition when the subject is imaged can be applied to the imaging of the reference member more precisely. Therefore, by imaging the reference member, the illumination condition for the subject can be determined more precisely.

The shape diagnostic apparatus 1100 includes: an actual subject image acquisition unit 1022 that acquires an actual subject image that is an image of a subject taken by the first illumination condition; a reference member image acquisition unit 1010 that acquires a reference member image that is an image of a reference member having a plurality of normal directions taken under the first illumination condition; a three-dimensional shape acquisition unit 1018 that acquires original three-dimensional shapes and optical characteristics of the reference member and the subject; a normal direction determination unit 1014 that determines a normal direction of each region of the reference member image based on the three-dimensional shape of the reference member; an illumination condition storage unit 1016 that stores a color of the reference member image for every normal direction as the first illumination data representing the first illumination condition; a posture determination unit 1024 that determines a posture of the subject in the actual subject image based on the three-dimensional shape of the subject; a subject CG generation unit 1020 that generates a CG image of the subject in a case where the subject having the original three-dimensional shape is imaged in the determined posture under the first illumination condition, based on the original three-dimensional shape of the subject, the optical characteristics of the subject, the first illumination data and the posture of the subject in the actual subject image; and a defective region detection unit 1026 that compares the CG image of the subject with the actual subject image for each region and detects a region where a brightness difference exceeds a predetermined reference value as a defective region. The optical characteristics of the subject contain a specular reflection factor and surface roughness.

The shape diagnostic apparatus 1100 further includes a shape-of-defective-region determination unit 1028 that determines the normal direction corresponding to the color of the defective region from the first illumination data and determines the three-dimensional shape of the defective region based on the thus determined normal direction.

A recording medium 1060 stores a program for making the shape diagnostic apparatus 1100 execute functions of the reference member image acquisition unit 1010, normal direction determination unit 1014, illumination condition storage unit 1016, three-dimensional shape acquisition unit 1018, subject CG generation unit 1020, actual subject image acquisition unit 1022, posture determination unit 1024, defective region detection unit 1026 and shape-of-defective-region determination unit 1028. The shape diagnostic apparatus 1100 may acquire such a program via a network so as to execute it.

By the above structure, the shape diagnostic apparatus 1100 can determine the illumination condition for the actual subject image from the reference member image and can generate the CG image of the subject, in which the subject has the original three-dimensional shape and is in the same posture as that in the actual subject image, under the same illumination condition as that for the actual subject image. Then, the shape diagnostic apparatus 1100 can detect a region of the actual subject image, where a brightness difference between the actual subject image and the CG image exceeds a predetermined reference value, as a defective region where the shape has a defect. Moreover, the shape diagnostic apparatus 1100 can determine the three-dimensional shape of the defective region.

Figure 9:
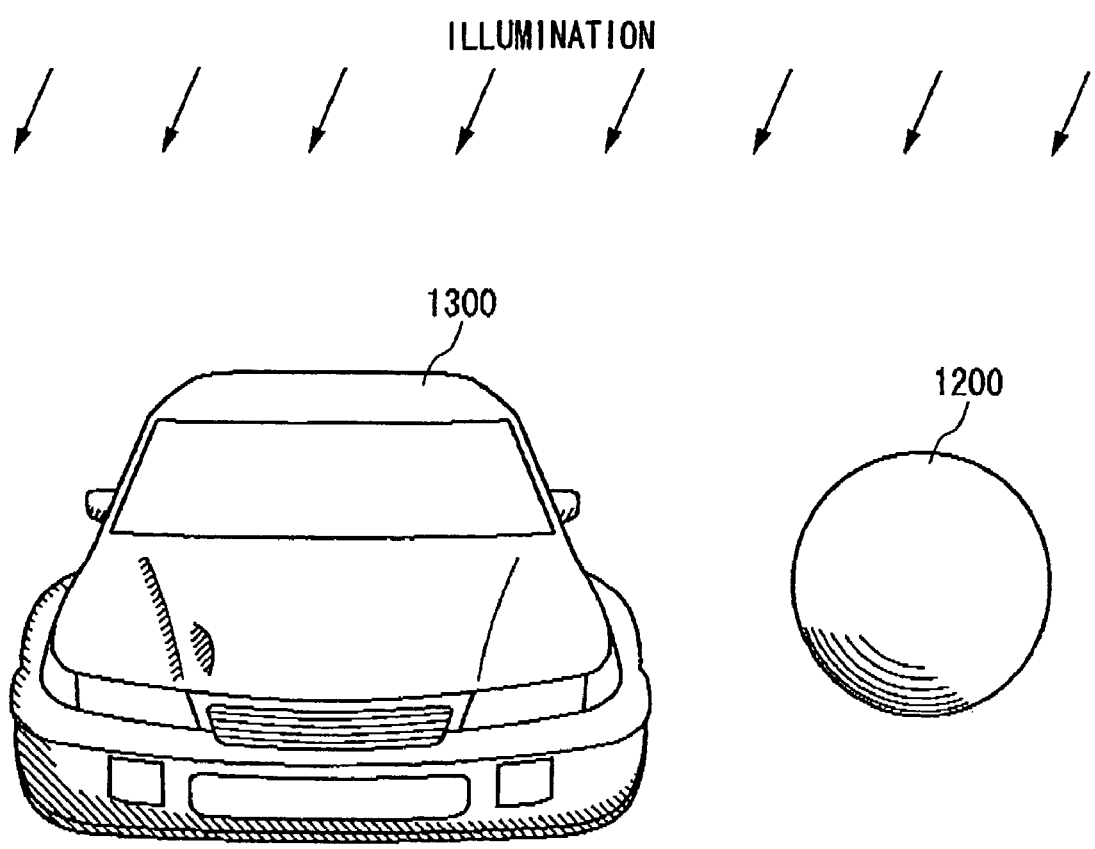
FIG. 9 shows imaging of a subject 1300 and a reference member 1200 under the first illumination condition.

FIG. 9 shows imaging of a subject 1300 and a reference member 1200 under a given illumination condition. This given illumination condition is an example of the first illumination condition. The reference member image acquisition unit 1010 and the actual subject image acquisition unit 1022 image the reference member 1200 and the subject 1300 under the same illumination condition, respectively. In this case, when a region of the reference member 1200 and a region of the subject 1300 have the same normal direction, the illumination condition for those regions is also the same. Therefore, the reference member image acquisition unit 1010 can acquire an image of the reference member 1200 (hereinafter, referred to as a reference member image) under the same illumination condition as that for the subject 1300.

In the shown example, the reference member 1200 and the subject 1300 are imaged simultaneously. However, the reference member 1200 may be imaged separately from the subject 1300, as long as it is imaged under the same illumination condition as that for the subject 1300. For example, the reference member 1200 may be imaged separately from the subject 1300 immediately before or after the imaging of the subject 1300.

Figure 10:
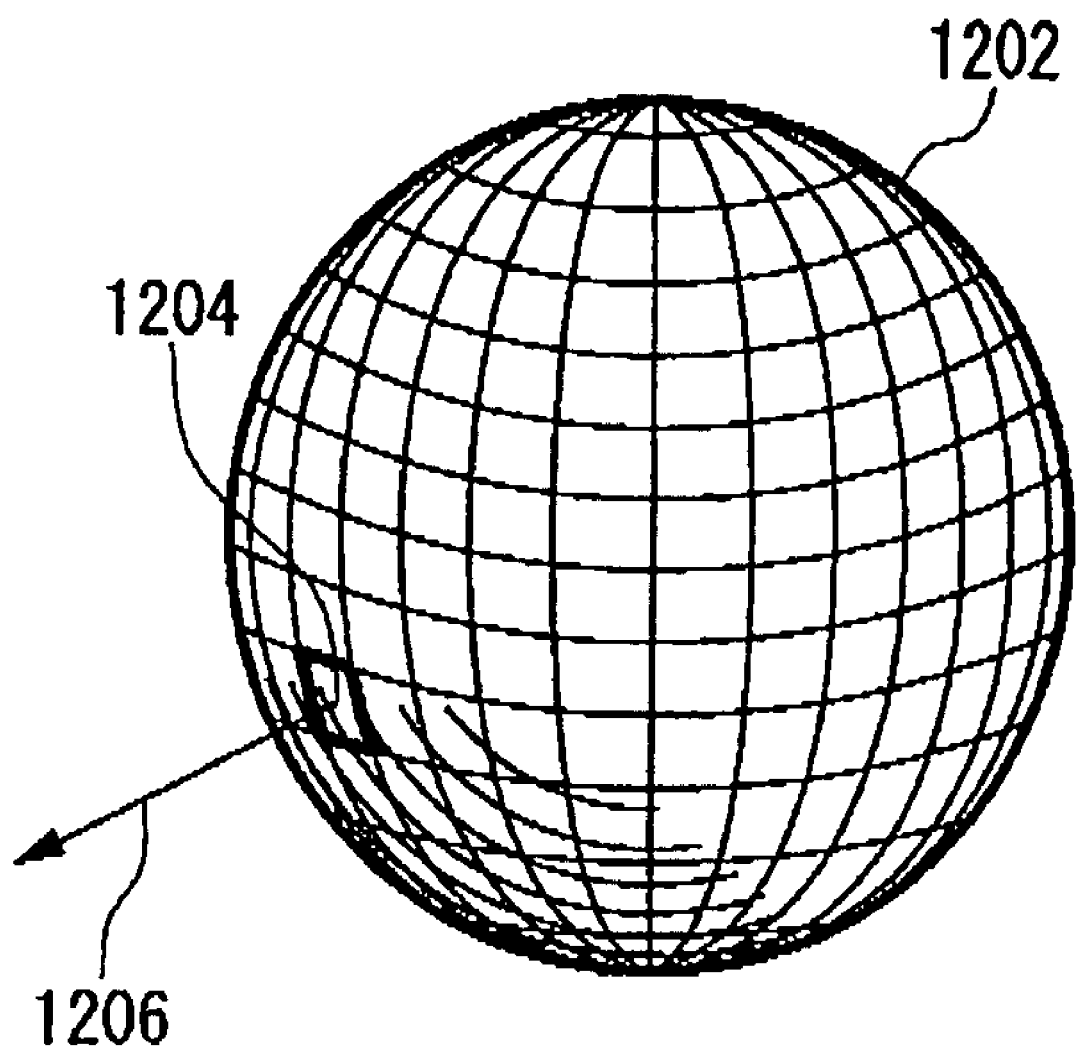
FIG. 10 shows an example of acquisition of a color of a "reference member image" for every normal direction as the first illumination data.

FIG. 10 shows an example in which brightness in the "reference member image" for every normal direction is acquired as the first illumination data. The first illumination data is the illumination condition for the subject 1300 described in FIG. 9 and represents brightness on a small plane depending on the normal direction. The normal direction determination unit 1014 acquires shape data of the reference member 1200 from the three-dimensional shape acquisition unit 1018 and superimposes the shape data on the reference member image 1202 in such a manner that the posture indicated by the shape data is coincident with the posture of the reference member in the reference member image 1202, thereby determining the normal direction of each region of the reference member image 1202. Since the reference member 1200 in the present embodiment is spherical, the shape of the reference member image 1202 is the same irrespective of the posture of the reference member 1200. Thus, the normal direction detection unit 1014 can superimpose the shape data on the reference member image 1202 easily without adjusting the orientation of the shape data with respect to the reference member image 1202.

The shape data representing the three-dimensional shape is wireframe data, for example. The wireframe data represents a shape of an object as collection of small planes and defines a normal direction of each small plane. The normal direction determination unit 1014 determines a normal direction defined for each small plane in the wireframe data as a normal direction of a corresponding region of the reference member image 1202. The format of the shape data is not limited to wireframe data. Polygon data, surface data, solid data and the like may be used, as long as it allows the normal direction of each region to be read out.

Next, the illumination condition storage unit 1016 measures brightness of each small plane of the reference member image 1202 and stores it to be associated with the corresponding normal direction. For example, the illumination condition storage unit 1016 stores brightness of the small plane 1204 to be associated with the direction of the normal 1206. In this manner, the illumination condition storage unit 1016 can measure brightness of each region of the subject 1300 depending on the normal direction equivalently from the reference member image 1202, as the first illumination data. The illumination condition storage unit 1016 stores the first illumination data in form of a table in which brightness of each small plane is recorded to be associated with the normal direction of that small plane, for example.

Figure 11A:
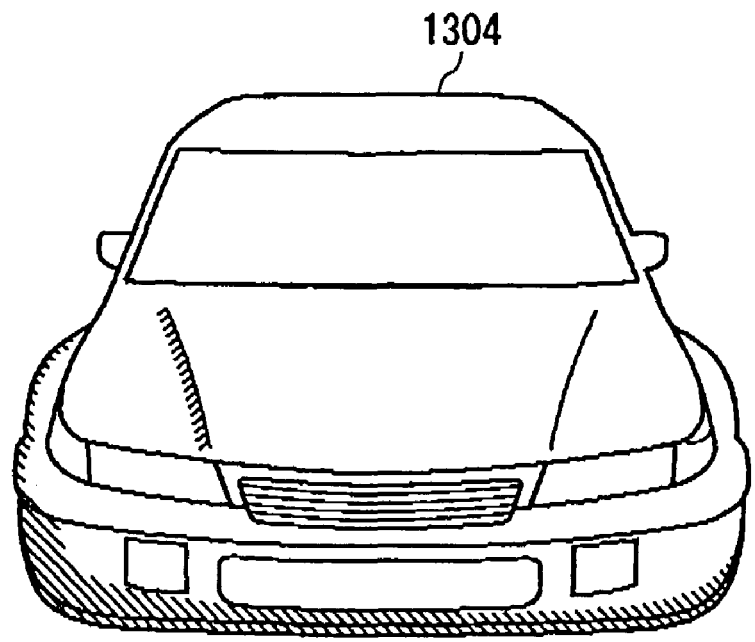
FIGS. 11A and 11B show an example of comparison of between an "actual subject image" and a "CG image" of the subject.
Figure 11B:
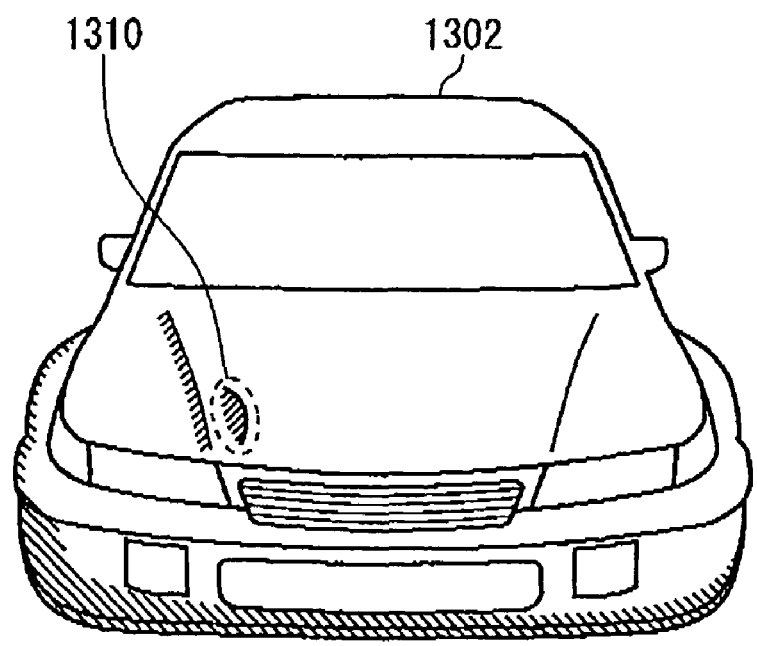

FIGS. 11A and 11B show comparison between the "actual subject image" and the "CG image". FIG. 11B shows the actual subject image 1302 that was taken by the actual subject image acquisition unit 1022, while FIG. 11A shows the CG image 1304 that is the same as the actual subject image 1302 in the posture of the subject and the illumination condition. The subject CG generation unit 1020 generates the CG image 1304 of the subject 1300 in which the subject has the original three-dimensional shape and is in the same posture as that in the actual subject image 1302, under the same illumination condition as that for the actual subject image 1302 based on the posture of the subject determined by the posture determination unit 1024 and the first illumination data stored in the illumination condition storage unit 1016. Then, the defective region detection unit 1026 compares brightness of the actual subject image 1302 with that of the CG image 1304 for every region so as to detect a region where a brightness difference exceeds a predetermined reference value as a defective region with respect to the shape. The brightness difference is a difference or a magnifying power of a value representing brightness, for example.

For example, in a case where brightness of a region 1310 of the actual subject image 1302 is smaller than that of the corresponding region of the CG image 1304 and the brightness difference exceeds a predetermined reference value, the defective region detection unit 1026 determines that region 1310 as the defective region and highlights that region 1310, for example, by drawing a circle around that region 1310. Then, the shape-of-defective-region determination unit 1028 reads out the normal direction corresponding to brightness of the region 1310 from the first illumination data stored in the illumination condition storage unit 1016, and determines the shape of the region 1310 based on a plane having the normal direction thus read out. The shape-of-defective-region determination unit 1028 displays the shape obtained as a result of the determination in form of mesh data or polygon data.

Figure 12:
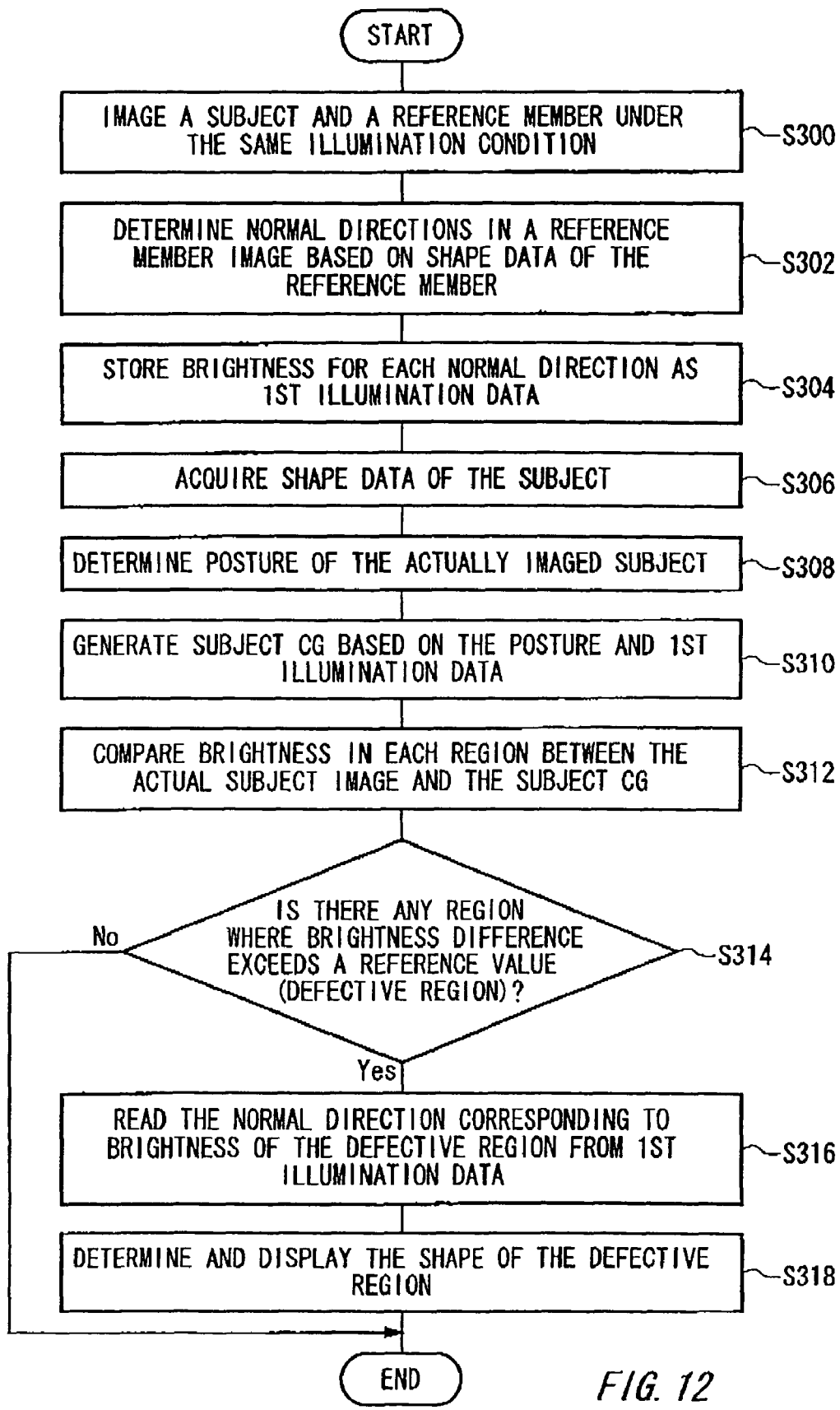
FIG. 12 is a flowchart for detecting a defect in the shape of the subject by using the "actual subject image".

FIG. 12 is a flowchart of a method for detecting a defect in the shape of the subject by using the "actual subject image". First, the actual subject image acquisition unit 1022 and the reference member image acquisition unit 1010 image the subject 1300 and the reference member 1200 under the same illumination condition so as to acquire an actual subject image 1302 and a reference member image 1202, respectively (Step S300).

Then, the normal direction determination unit 1014 acquires shape data of the reference member 1200 from the three-dimensional shape acquisition unit 1018 and superimposes that shape data on the reference member image 1202 in such a manner that the posture of the reference member in the shape data is coincident with that in the reference member image 1202, thereby determining a normal direction of each region of the reference member image 1202 (Step S302). Then, the illumination condition storage unit 1016 measures brightness of each region of the reference member image 1202 and stores it to be associated with the normal direction of that region as the first illumination data (Step S304).

On the other hand, the posture determination unit 1024 acquires shape data of the subject 1300 (Step S306) and determines the posture of the subject 1300 in the actual subject image 1302 acquired from the actual subject image acquisition unit 1022 (Step S308). In this determination, the posture determination unit 1024 determines the posture when the profile of the shape data is the most coincident with the actual subject image 1302, as the posture of the subject in the actual subject image 1302.

Next, the subject CG generation unit 1020 acquires the shape data and optical characteristics of the subject 1300 from the three-dimensional shape acquisition unit 1018, and generates a CG image 1304 of the subject based on the posture determined in Step S308 and the first illumination data stored in the illumination data storage unit 1016 (Step S310). In this generation, the subject CG generation unit 1020 determines brightness of each region of the CG image 1304 by reading out brightness that corresponds to the normal direction of each region of the CG image 1304 from the first illumination data.

Then, the defective region detection unit 1026 compares brightness of each region of the actual subject image 1302 acquired from the actual subject image acquisition unit 1022 with brightness of the corresponding region of the CG image 1304 of the subject acquired from the subject CG generation unit 1020 (Step S312), so as to determine whether or not there is a region where a brightness difference exceeds a predetermined reference value (defective region) (Step S314). In a case where it was determined that there was no defective region (Step S314: No), the shape diagnostic apparatus 1100 displays that there is no defect in the shape of the subject 1300. That is the end of this flow.

On the other hand, in a case where it was determined there was a defective region (Step S314: Yes), the defective region detection unit 1026 highlights that defective region. The shape-of-defective-region determination unit 1028 reads out the normal direction that corresponds to brightness of the defective region from the first illumination data stored in the illumination condition storage unit 1016 (Step S316), and determines the shape of the defective region under a condition of constraint where a plane having the normal direction thus read out continues. Then, the shape-of-defective-region determination unit 1028 displays the shape as a result of the determination in form of mesh data or polygon data, for example (Step S318). That is the end of this flow.

In this embodiment, the shape diagnostic apparatus 1100 stored brightness of each region of the reference member image for every normal direction as data indicating the first illumination condition. However, the shape diagnostic apparatus 1100 may store the first illumination condition in the illumination condition storage unit 1016 in advance. For example, in a space where the same illumination condition can be maintained, such as a car repair shop, calculating the illumination condition every time the subject is imaged is unproductive. Thus, the shape diagnostic apparatus 1100 stores the number of light sources, the position of the light source, spectral components of light emitted from the light source and the directivity of the light in the illumination condition storage unit 1016 in advance, as the illumination condition for imaging the subject. The subject CG generation unit 1020 acquires the posture of the subject in the actual subject image from the posture determination unit 1024 and acquires the original three-dimensional shape and optical characteristics of the subject from the three-dimensional shape acquisition unit 1018. The subject CG generation unit 1020 then reads out the number of light sources, the position of the light source, spectral components of light emitted from the light source and the directivity of that light from the illumination condition storage unit 1016 as the illumination condition. Then, the subject CG generation unit 1020 generates the CG image of the subject based on the posture of the subject, the illumination condition, and the original three-dimensional shape and optical characteristics of the subject that were acquired. The operation of the defective region detection unit 1026, in which the actual subject image is compared with the CG image so as to detect the defective region of the subject, is the same as that described above. Therefore, the description of that operation is omitted.

Figure 13:
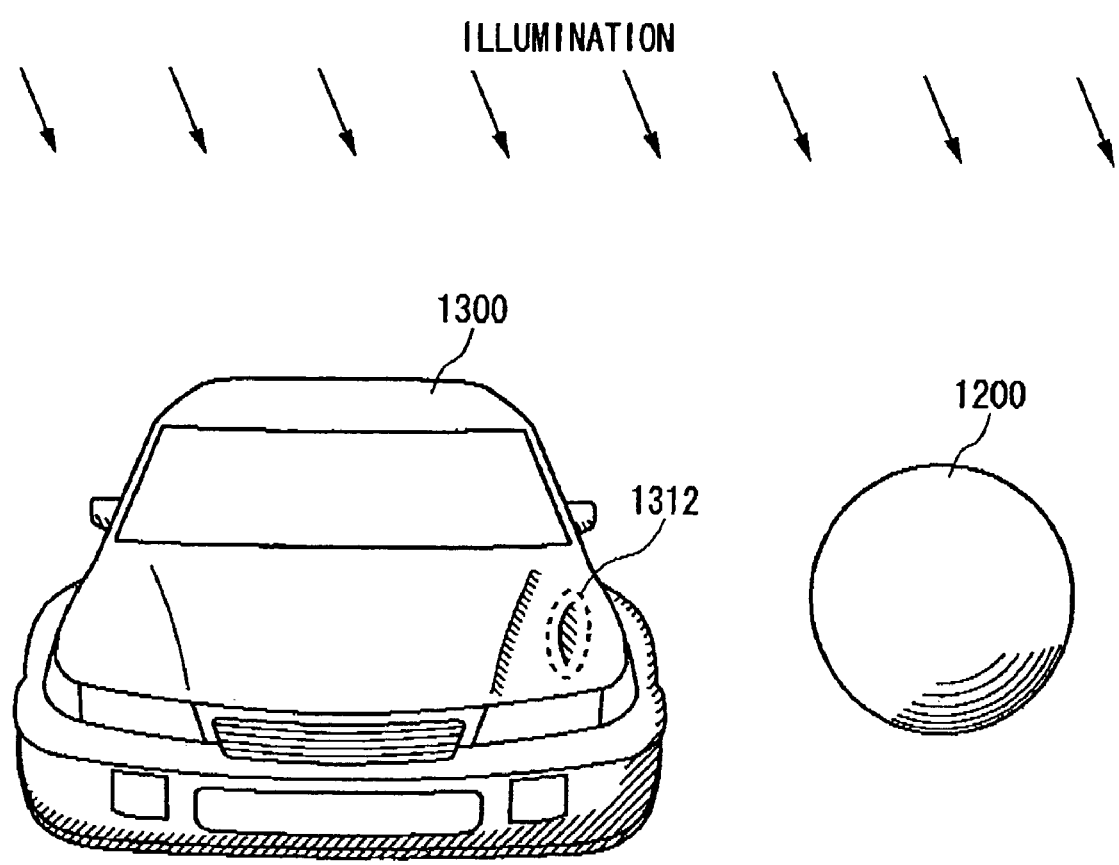
FIG. 13 shows imaging of the subject 1300 and the reference member 1200 under the second illumination condition.

FIG. 13 shows imaging of the subject 1300 and the reference member 1200 under the second illumination condition. The second illumination condition is different from the first illumination condition in the aforementioned example in the direction of illumination. It is preferable that the direction of illumination in the second illumination condition is perpendicular to that in the first illumination condition. Thus, it is possible to illuminate a region that is not illuminated with light under the first illumination condition, with light efficiently under the second illumination condition. In this case, the illumination condition storage unit 1016 stores the number of the light sources, the position of the light source, spectral components of light emitted from the light source and the directivity of that light as the second illumination condition in advance. The actual subject image acquisition unit 1022 further acquires the second actual subject image that is an image of the subject taken under the second illumination condition stored in the illumination storage unit 1016. The posture determination unit 1024 further determines the posture of the subject in the second actual subject image based on the original three-dimensional shape of the subject. The subject CG generation unit 1020 further generates the second CG image of the subject based on the posture of the subject in the second actual subject image, the second illumination condition, and the optical characteristics and original three-dimensional shape of the subject. The defective region detection unit 1026 further compares the second CG image of the subject with the second actual subject image for each region so as to further detect a region where a brightness difference exceeds a predetermined reference value as a defective region. In this manner, the shape diagnostic apparatus 1100 acquires the second actual subject image taken under the second illumination condition that is different from the first illumination condition in the direction of illumination. Thus, the shape diagnostic apparatus 1100 can acquire an image in which no underexposure or overexposure is contained for a wider region of the subject. Therefore, it is possible to detect the defect in the surface shape of the subject, such as a dent 1312, without exception.

For the optical characteristics of the subject, it is desirable that a specular reflection factor of the subject be low, i.e., a diffuse reflection factor be high. In a case where the diffuse reflection factor is high, components of specular reflection of illumination can be reduced, thus an actual image of the subject with no overexposure can be obtained. Next, a method for increasing the diffusion reflection factor of the subject is described.

Figure 14:
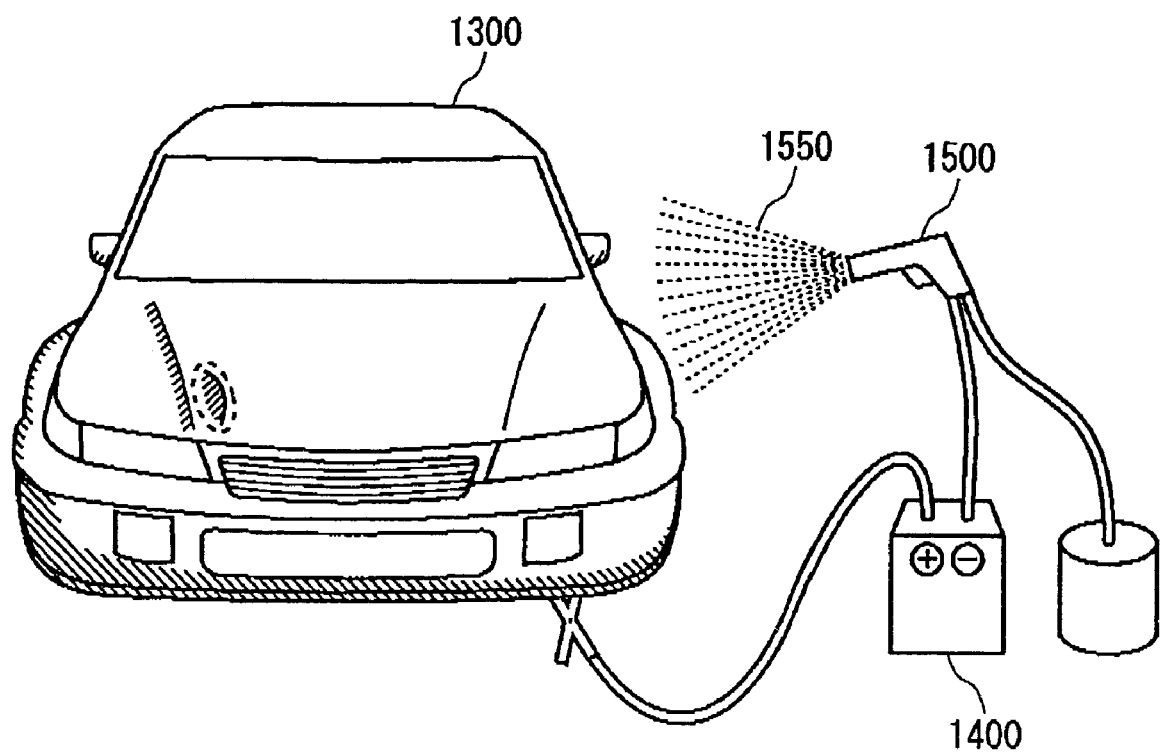
FIG. 14 shows how to make colored particles 1550 adhere to the subject 1300.

FIG. 14 shows how to make colored particles 1550 adhere to the subject 1300. The colored particles 1550 are particles of white or black electrostatic toner, for example, and have a nature of being attracted toward a charged object so as to adhere to that charged object. A charge device 1400 as an exemplary charge unit of the present invention charges the subject 1300 by a plug connected to the subject 1300. A particle spray device 1500 as an exemplary spray unit of the present invention is an air gun that sprays particles by using a compressed air supplied from a compressor, for example. The particle spray device 1500 sprays the colored particles 1550 toward the entire subject 1300. The colored particles 1550 are attracted toward a charged portion of the subject 1300 so as to adhere to the charged portion, thereby increasing the diffusion reflection factor. The actual subject image acquisition unit 1022 images the subject 1300 with the colored particles 1550 adhering thereto, so as to further acquire the third actual subject image. The subject in the third actual subject image has the increased diffusion reflection factor by adhesion of the colored particles 1550 to the subject. Thus, the actual subject image acquisition unit 1022 can acquire an image that includes no overexposure region and shows luminance depending on the normal direction of the subject as the third actual subject image.

The subject CG generation unit 1020 acquires the optical characteristics of the subject 1300 in a state in which the colored particles 1550 adhere to the subject 1300. The optical characteristics of the object with the colored particles 1550 are determined by absorption spectra of the colored particles 1550. Thus, the subject CG generation unit 1020 may store the optical characteristics of the subject with the colored particles 1550 in accordance with the type of the colored particles 1550. The subject CG generation unit 1020 acquires the posture of the subject in the third actual subject image from the posture determination unit 1024, acquires the illumination condition when the third actual subject image was taken from the illumination condition storage unit 1016, and acquires the three-dimensional shape of the subject 1300 from the three-dimensional shape acquisition unit 1018. Then, the subject CG generation unit 1020 generates the third CG image of the subject 1200 based on the posture of the subject, the illumination condition, the three-dimensional shape of the subject and the optical characteristics of the subject with the colored particles 1550 that were acquired. Then, the defective region determination unit 1028 compares the third CG of the subject 1300 with the third actual subject image for each region and detects a region where a brightness difference exceeds a predetermined reference value as the defective region. According to this example, it is possible to detect the defect in the surface shape of the subject, such as a dent, without exception by using the actual subject image obtained by imaging the subject with the increased diffusion reflection factor.

As is apparent from the above description, according to the present embodiment, it is possible to detect a defect in the shape of the subject 1300 based on the actual image of the subject 1300.

Although the present invention has been described by way of exemplary embodiments, it should be understood that those skilled in the art might make many changes and substitutions without departing from the spirit and the scope of the present invention which is defined only by the appended claims.

What is claimed is:

1. An image processing apparatus for correcting an image of a subject, comprising:
    a first illuminated image capture unit operable to capture a first reference member image that is an image of a reference member having a plurality of normal directions taken under a first illumination condition;
    a second illuminated image capture unit operable to capture a second reference member image that is an image of said reference member taken under a second illumination condition, and a subject image that is an image of a given subject taken under said second illumination condition;
    a shape capture unit operable to capture three-dimensional shapes of said reference member and said subject;
    a normal direction determination unit operable to determine a normal direction of each region in said first reference member image, said second reference member image and said subject image based on said three-dimensional shapes of said reference member and said subject;
    a difference calculation unit operable to calculate a color difference in each region between said first and second reference member images for every normal direction; and
    a subject image correction unit operable to correct a color of each region in said subject image with said color difference for every normal direction.

2. An image processing apparatus as claimed in claim 1, wherein said reference member is spherical.

3. An image processing apparatus as claimed in claim 1, wherein said reference member and said subject have substantially the same optical characteristics.

4. An image processing apparatus as claimed in claim 1, wherein said first illuminated image capture unit captures said first reference member image under an illumination condition that is ideal for imaging said subject as said first illumination condition.

5. An image processing apparatus for correcting an image of a subject, comprising:
    a first illuminated image capturing unit operable to capture a first reference member image with a first material color under a first illumination condition, said first reference member image being a three-dimensional image of a reference member having a plurality of normal directions;
    a second illuminated image capture unit operable to capture a subject image that is an image of a given real subject taken under a second illumination condition that is a given real illumination condition, and a second reference member image that is an image of said reference member having the same color as said subject taken under said second illumination condition;
    a shape capture unit operable to capture three-dimensional shapes of said reference member and said subject;
    a normal direction determination unit operable to determine a normal direction of each region in said first reference member image, said second reference member image and said subject image based on said three-dimensional shapes of said reference member and said subject;
    a difference calculation unit operable to calculate a color difference in each region between said first and second reference member images for every normal direction; and
    a subject image correction unit operable to correct a color of each region of said subject image with said color difference for every normal direction.

6. An image processing method for correcting an image of a subject, comprising:
    capturing a first reference member image that is an image of a reference member having a plurality of normal directions under a first illumination condition;
    capturing a second reference member image that is an image of said reference member taken under a second illumination condition, and a subject image that is an image of a given subject under said second illumination condition;
    capturing three-dimensional shapes of said reference member and said subject;
    determining a normal direction of each region in said first reference member image, said second reference member image and said subject image based on said three-dimensional shapes of said reference member and said subject;
    calculating a color difference in each region between said first and second reference member images for every normal direction; and
    correcting a color of each region of said subject image with said color difference for every normal direction.

7. An image processing method for correcting an image of a subject, comprising:
    capturing a first reference member image with a first material color under a first illumination condition, said first reference member image being a three-dimensional image of a reference member having a plurality of normal directions;
    capturing a subject image that is an image of a given real subject taken under a second illumination condition that is a given real illumination condition, and a second reference member image that is an image of said reference member having the same color as said subject, taken under said second illumination condition;
    capturing three-dimensional shapes of said reference member and said subject;
    determining a normal direction of each region in said first reference member image, said second reference member image, and said subject image based on said three-dimensional shapes of said reference member and said subject;
    calculating a color difference in each region between said first and second reference member images for every normal direction; and correcting a color of each region of said subject image with said color difference for every normal direction.

8. A tangible non-transitory computer readable medium encoded with a program for use in a computer for correcting an image of a subject, wherein said program makes said computer execute functions of:
  capturing a first reference member image that is an image of a reference member having a plurality of normal directions taken under a first illumination condition;
  capturing a second reference member image that is an image of said reference member taken under a second illumination condition, and a subject image that is an image of a given subject under said second illumination condition;
  capturing three-dimensional shapes of said reference member and said subject;
  determining a normal direction of each region in said first reference member image, said second reference member image and said subject image based on said three-dimensional shapes of said reference member and said subject;
  calculating a color difference in each region between said first and second reference member images for every normal direction; and
  correcting a color in each region of said subject image with said color difference for every normal direction.

9. A tangible non-transitory computer readable medium encoded with a program for use in a computer for correcting an image of a subject, wherein said program makes said computer execute functions of:
  capturing a first reference member image with a first material color under a first illumination condition, said first reference member image being a three-dimensional image of a reference member having a plurality of normal directions;
  capturing a subject image that is an image a given real subject taken under a second illumination condition that is a given real illumination condition, and a second reference member image that is an image of said reference member having the same color as said subject, taken under said second illumination condition;
  capturing three-dimensional shapes of said reference member and said subject;
  determining a normal direction of each region in said first reference member image, said second reference member image, and said subject image based on said three-dimensional shapes of said reference member and said subject;
  calculating a color difference in each region between said first and second reference member images for every normal direction; and
  correcting a color of each region of said subject image with said color difference for every normal direction.

10. An image processing apparatus as claimed in claim 1, wherein the difference calculation unit calculates the color difference by calculating a difference in chromaticity and a difference in color saturation in each region between said first and second reference images for every normal direction.

11. An image processing apparatus for correcting an image of a subject, comprising:
  a first illuminated image generation unit operable to generate a first reference member image with a first material color under a first illumination condition, said first reference member image being a three-dimensional image of a reference member having a plurality of normal directions;
  a second illuminated image capture unit operable to capture a subject image that is an image of a given real subject taken under a second illumination condition that is a given real illumination condition, and a second reference member image that is an image of said reference member having the same color as said subject taken under said second illumination condition;
  a shape capture unit operable to capture three-dimensional shapes of said reference member and said subject;
  a normal direction determination unit operable to determine a normal direction of each region in said first reference member image, said second reference member image and said subject image based on said three-dimensional shapes of said reference member and said subject;
  a difference calculation unit operable to calculate a color difference in each region between said first and second reference member images for every normal direction; and
  a subject image correction unit operable to correct a color of each region of said subject image with said color difference for every normal direction, wherein the difference calculation unit calculates the color difference by calculating a difference in chromaticity and a difference in color saturation in each region between said first and second reference images for every normal direction.

12. An image processing method as claimed in claim 6, wherein the color difference is calculated by calculating a difference in chromaticity and a difference in color saturation in each region between said first and second reference images for every normal direction.

13. An image processing method for correcting an image of a subject, comprising:
  generating a first reference member image with a first material color under a first illumination condition, said first reference member image being a three-dimensional image of a reference member having a plurality of normal directions;
  capturing a subject image that is an image of a given real subject taken under a second illumination condition that is a given real illumination condition, and a second reference member image that is an image of said reference member having the same color as said subject, taken under said second illumination condition;
  capturing three-dimensional shapes of said reference member and said subject;
  determining a normal direction of each region in said first reference member image, said second reference member image, and said subject image based on said three-dimensional shapes of said reference member and said subject;
  calculating a color difference in each region between said first and second reference member images for every normal direction; and
  correcting a color of each region of said subject image with said color difference for every normal direction, wherein the color difference is calculated by calculating a difference in chromaticity and a difference in color saturation in each region between said first and second reference images for every normal direction.

14. the tangible computer readable medium as claimed in claim 8, wherein the color difference is calculated by calculating a difference in chromaticity and a difference in color saturation in each region between said first and second reference images for every normal direction.

15. A tangible non-transitory computer readable medium encoded with a program for use in a computer for correcting an image of a subject, wherein said program makes said computer execute functions of:

generating a first reference member image with a first material color under a first illumination condition, said first reference member image being a three-dimensional image of a reference member having a plurality of normal directions;

capturing a subject image that is an image a given real subject taken under a second illumination condition that is a given real illumination condition, and a second reference member image that is an image of said reference member having the same color as said subject, taken under said second illumination condition;

capturing three-dimensional shapes of said reference member and said subject;

determining a normal direction of each region in said first reference member image, said second reference member image, and said subject image based on said three-dimensional shapes of said reference member and said subject;

calculating a color difference in each region between said first and second reference member images for every normal direction; and correcting a color of each region of said subject image with said color difference for every normal direction, wherein the color difference is calculated by calculating a difference in chromaticity and a difference in color saturation in each region between said first and second reference images for every normal direction.

* * * * *